United States Patent
Sasaki

(10) Patent No.: US 10,730,761 B2
(45) Date of Patent: Aug. 4, 2020

(54) TREATMENT METHOD OF AN AQUEOUS SOLUTION CONTAINING UREA, AMMONIA AND CARBON DIOXIDE AND TREATMENT EQUIPMENT THEREFOR

(71) Applicant: TOYO ENGINEERING CORPORATION, Chiyoda-ku, Tokyo (JP)

(72) Inventor: Keigo Sasaki, Narashino (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 58 days.

(21) Appl. No.: 16/208,332

(22) Filed: Dec. 3, 2018

(65) Prior Publication Data
US 2019/0177180 A1  Jun. 13, 2019

(30) Foreign Application Priority Data
Dec. 8, 2017 (JP) .................. 2017-235912

(51) Int. Cl.
| | | |
|---|---|---|
| *B01D 19/00* | (2006.01) | |
| *B01D 3/14* | (2006.01) | |
| *B01D 3/38* | (2006.01) | |
| *B01D 53/58* | (2006.01) | |
| *B01D 53/78* | (2006.01) | |
| *C01C 1/28* | (2006.01) | |

(Continued)

(52) U.S. Cl.
CPC .............. *C02F 1/025* (2013.01); *B01D 3/009* (2013.01); *B01D 3/143* (2013.01); *B01D 3/38* (2013.01); *B01D 19/001* (2013.01); *B01D 53/78* (2013.01); *C02F 1/20* (2013.01); *C07C 273/02* (2013.01); *C02F 2101/16* (2013.01); *C02F 2103/36* (2013.01); *C02F 2209/02* (2013.01); *C02F 2209/03* (2013.01); *C02F 2301/08* (2013.01)

(58) Field of Classification Search
CPC .......... B01D 3/00; B01D 3/009; B01D 3/143; B01D 3/38; B01D 19/001; B01D 53/58; B01D 53/78; C01C 1/28; C02F 1/025; C02F 1/20; C02F 1/66; C02F 2101/16; C02F 2101/38; C02F 2103/36; C02F 2209/02; C02F 2209/03; C02F 2301/08; C07C 273/00; C07C 273/02
See application file for complete search history.

(56) References Cited

FOREIGN PATENT DOCUMENTS

| | | |
|---|---|---|
| JP | S5352274 A | 5/1978 |
| JP | 2000001466 A | 1/2000 |

*Primary Examiner* — Lucas A Stelling
(74) *Attorney, Agent, or Firm* — Law Office of Katsuhiro Arai

(57) ABSTRACT

Disclosed are: a treatment method comprising (1) a step in which an aqueous solution containing urea, ammonia and carbon dioxide is introduced into a first stripper (PCS1) and subjected to stripping, and the aqueous solution after stripping is introduced into a urea hydrolyzer (UHY), (2) a step in which urea in the aqueous solution is hydrolyzed in the urea hydrolyzer (UHY), and the aqueous solution after hydrolysis is introduced into a second stripper (PCS2), (3) a step in which the aqueous solution is subjected to stripping in the second stripper (PCS2), and (4) a step in which a part of the aqueous solution before being stripped in the first stripper (PCS1), and/or, a part of the aqueous solution after being stripped in the first stripper (PCS1) but before being hydrolyzed in the urea hydrolyzer (UHY) is introduced into an exhaust gas treatment equipment equipped with an ammonia scrubbing equipment (ASCR); and a treatment equipment therefor.

22 Claims, 3 Drawing Sheets

(51) Int. Cl.
*C02F 1/02* (2006.01)
*C02F 1/20* (2006.01)
*C02F 1/66* (2006.01)
*C07C 273/02* (2006.01)
*B01D 3/00* (2006.01)
*C02F 101/16* (2006.01)
*C02F 103/36* (2006.01)

TREATMENT METHOD OF AN AQUEOUS SOLUTION CONTAINING UREA, AMMONIA AND CARBON DIOXIDE AND TREATMENT EQUIPMENT THEREFOR

TECHNICAL FIELD

The present invention relates to a treatment method in which urea in an aqueous solution containing urea, ammonia and carbon dioxide is hydrolyzed and ammonia and carbon dioxide in the aqueous solution are separated and recovered; and a treatment equipment therefor. More specifically, the present invention relates to a treatment method in which it is possible to reduce the amount of heating steam and make the equipment compact by lowering the load of a urea hydrolyzer without lowering the hydrolysis efficiency of urea, and furthermore, emission of ammonia into atmospheric air is suppressed even if a part of the aqueous solution is introduced into an exhaust gas treatment equipment of a urea production equipment; and a treatment equipment therefor.

BACKGROUND ART

A urea synthesis solution obtained by reacting ammonia and carbon dioxide under high temperature and high pressure contains urea generated, water, unreacted ammonia and carbon dioxide. The urea synthesis solution is subjected to stripping or distillation sequentially under reduced pressure to separate unreacted substances, and unreacted ammonia and carbon dioxide are respectively contained in an amount of about 1% by mass or less before entering the concentration step, while the water content is 20 to 40% by mass. In the concentration step, water in the urea synthesis solution is evaporated. However, a small amount of unreacted ammonia and carbon dioxide are also contained in the drainage (evaporated water) of this concentration step. In addition, there are many cases where also urea is mixed even though it is slight. Therefore, a treatment to recover each component from the drainage containing urea, unreacted ammonia and carbon dioxide is required.

For example, Patent Document 1 discloses a treatment method consisting of a step in which an aqueous solution containing urea, ammonia and carbon dioxide is stripped in a first stripper to separate ammonia and carbon dioxide, thereby obtaining a urea aqueous solution containing substantially no ammonia, a step in which urea in this urea aqueous solution is hydrolyzed and a step in which the aqueous solution after hydrolysis is stripped in a second stripper to separate ammonia and carbon dioxide.

The treatment method of Patent Document 1 specifically includes the steps shown in FIG. 3. First, drainage consisting of urea (U), ammonia (N), carbon dioxide (C) and water (H) is introduced into a first stripper (PCS1) from a process condensate tank (PCT). By stripping with this first stripper (PCS1), ammonia (N) and carbon dioxide (C) are separated and discharged as a gas. The drainage consisting of urea (U) and water (H) after stripping (however, also trace amount of ammonia (N) actually remains) is introduced into a urea hydrolyzer (UHY). In this urea hydrolyzer (UHY), urea (U) is hydrolyzed to give ammonia (N) and carbon dioxide (C). Then, the drainage consisting of ammonia (N), carbon dioxide (C) and water (H) after hydrolysis is introduced into a second stripper (PCS2). Here, ammonia (N) and carbon dioxide (C) are separated by performing stripping again. As illustrated in the drawings of Patent Document 1, the first stripper (PCS1) and the second stripper (PCS2) are respectively arranged as an upper region and a lower side region of one tower, and ammonia (N) and carbon dioxide (C) separated in the second stripper (PCS2) are introduced into the upper first stripper (PCS1).

In addition, the urea hydrolyzer (UHY) requires to be given the heat necessary for the hydrolysis reaction. Thus, in Patent Document 1, heating steam (STM) is supplied to the urea hydrolyzer (UHY). Further, in Patent Document 1, the first stripper (PCS1) and the second stripper (PCS2) are arranged as an upper region and a lower region of one tower, and indirect heating using a reboiler and low pressure steam and direct heating by low pressure steam and steam from the second stripper are explained for the first stripper (PCS1) and direct heating by low pressure steam and indirect heating using a reboiler are explained for the second stripper (PCS2).

Patent Document 1 describes an effect that the hydrolysis efficiency of urea in the urea hydrolyzer (UHY) is improved since ammonia (N) and carbon dioxide (C) are separated in the first stripper (PCS1) before hydrolyzing urea (U) in the urea hydrolyzer (UHY). It is also described as one object of the invention to reduce the amount of heating steam necessary for processing.

In this treatment method of Patent Document 1, the hydrolysis efficiency in the urea hydrolyzer (UHY) is improved, and as a result, the amount of heating steam (STM) supplied to the urea hydrolyzer (UHY) is reduced. In particular, as compared with heating steam (STM) supplied to each stripper, heating steam (STM) supplied to the urea hydrolyzer (UHY) has higher temperature and higher pressure, so it is very important to reduce the use amount thereof. Therefore, if it is possible to further improve the treatment method of Patent Document 1 and to find a method of further reducing the amount of heating steam (STM) with high temperature and high pressure, it would be a very useful invention in the industry.

On the other hand, a method to recover ammonia in a gas discharged from the granulation step is known, for reducing emission of ammonia generated from a urea granulation step using a prill urea granulation equipment or a urea granulation equipment using a rotary drum, a fluidized bed or a fluidized-spouted bed into atmospheric air. For example, Patent Document 2 describes a method in which a gas containing urea dust and ammonia generated from a urea granulation equipment is introduced into a first scrubbing tower (corresponding to urea dust scrubbing equipment) in which a urea aqueous solution circulates, where the urea dust is chiefly recovered, then, the urea dust-recovered gas is introduced into a second scrubbing tower (corresponding to acid scrubbing equipment to be described later) in which an acid-containing water circulates, where ammonia is recovered.

In the urea dust scrubbing equipment, water is evaporated together with discharged air, so it is necessary to supply water from the outside. As water to be supplied to it, water generated as a by-product of urea synthesis is usually used. However, ammonia is contained in the water obtained by concentrating the urea synthesis solution, and if this water is supplied to the urea dust scrubbing equipment as it is, the amount of ammonia emitted into atmospheric air will undesirably increase. Therefore, it is usual to use water after treating with a stripper and a urea hydrolyzer, that is, water after thoroughly removing ammonia. The reason why the urea hydrolyzer is used here is that it is difficult to sufficiently remove ammonia in the presence of urea in water.

That is, conventionally, it is usual to use water after treatment with at least a urea hydrolyzer as water to be supplied to the urea dust scrubbing equipment, and the idea of using water before treating with a urea hydrolyzer is not common.

RELATED ART DOCUMENTS

Patent Documents

Patent Document 1: JP S53-52274
Patent Document 2: JP 2000-001466

SUMMARY OF INVENTION

Technical Problem

The present invention has been made to solve the problems of the above-described conventional techniques. That is, the object of the present invention is to provide a treatment method and a treatment equipment in which it is possible to reduce the amount of heating steam and make the equipment compact by lowering the load of the apparatus such as a urea hydrolyzer without lowering the hydrolysis efficiency of urea, and furthermore, emission of ammonia into atmospheric air is suppressed even if a part of the aqueous solution (for example, drainage generated from the concentration step of a urea synthesis solution) is introduced into an exhaust gas treatment equipment of a urea production equipment.

Solution to Problem

The present invention is a treatment method of an aqueous solution containing urea, ammonia and carbon dioxide in which urea in the aqueous solution containing urea, ammonia and carbon dioxide is hydrolyzed and ammonia and carbon dioxide in the aqueous solution are separated and recovered, wherein the treatment method comprises (1) a step in which an aqueous solution containing urea, ammonia and carbon dioxide is introduced into a first stripper and subjected to stripping, thereby separating and recovering ammonia and carbon dioxide in the aqueous solution, and the aqueous solution after stripping is introduced into a urea hydrolyzer, (2) a step in which the aqueous solution introduced into the urea hydrolyzer is heated under pressure, thereby hydrolyzing urea in the aqueous solution, and the aqueous solution after hydrolysis is introduced into a second stripper, (3) a step in which the aqueous solution introduced into the second stripper is subjected to stripping, thereby separating ammonia and carbon dioxide in the aqueous solution, and (4) a step in which a part of the aqueous solution before being stripped in the first stripper, and/or, a part of the aqueous solution after being stripped in the first stripper but before being hydrolyzed in the urea hydrolyzer is introduced into an exhaust gas treatment equipment equipped with a urea dust scrubbing equipment and an equipment to suppress emission of ammonia.

Further, the present invention is a treatment equipment of an aqueous solution containing urea, ammonia and carbon dioxide in which urea in the aqueous solution containing urea, ammonia and carbon dioxide is hydrolyzed and ammonia and carbon dioxide in the aqueous solution are separated and recovered, wherein the treatment equipment has a first stripper to subject an aqueous solution containing urea, ammonia and carbon dioxide to stripping, thereby separating ammonia and carbon dioxide in the aqueous solution, a pipe to recover a gas containing ammonia and carbon dioxide separated by stripping in the first stripper, a pipe to introduce the aqueous solution after stripping in the first stripper into a urea hydrolyzer, a urea hydrolyzer to heat under pressure the aqueous solution after stripping introduced from the first stripper, thereby hydrolyzing urea in the aqueous solution, a pipe to introduce the aqueous solution after hydrolysis in the urea hydrolyzer into a second stripper, a second stripper to subject the aqueous solution after hydrolysis in the urea hydrolyzer to stripping, thereby separating ammonia and carbon dioxide in the aqueous solution, and a pipe to introduce a part of the aqueous solution before being stripped in the first stripper, and/or, a part of the aqueous solution after being stripped in the first stripper but before being hydrolyzed in the urea hydrolyzer into an exhaust gas treatment equipment equipped with a urea dust scrubbing equipment and an equipment to suppress emission of ammonia.

Further, the present invention is an improvement method of a treatment equipment of an aqueous solution containing urea, ammonia and carbon dioxide, to lower the equipment load of the treatment equipment in which urea in the aqueous solution containing urea, ammonia and carbon dioxide is hydrolyzed and ammonia and carbon dioxide in the aqueous solution are separated and recovered, and to effectively utilize a part of the aqueous solution, wherein an existing treatment equipment has a first stripper to subject an aqueous solution containing urea, ammonia and carbon dioxide to stripping, thereby separating ammonia and carbon dioxide in the aqueous solution, a urea hydrolyzer to heat under pressure the aqueous solution after stripping introduced from the first stripper, thereby hydrolyzing urea in the aqueous solution, and a second stripper to subject the aqueous solution after hydrolysis in the urea hydrolyzer to stripping, thereby separating ammonia and carbon dioxide in the aqueous solution; and, the improvement method comprises adding a pipe to the existing treatment equipment in which the pipe is for introducing at least a part of the aqueous solution before being stripped in the first stripper, and/or, a part of the aqueous solution after being stripped in the first stripper but before being hydrolyzed in the urea hydrolyzer into an exhaust gas treatment equipment equipped with a urea dust scrubbing equipment and an equipment to suppress emission of ammonia.

Further, the present invention is a production method of granular urea which comprises a step of introducing a gas containing urea dust and ammonia generated from a urea granulation equipment into an exhaust gas treatment equipment equipped with a urea dust scrubbing equipment and an equipment to suppress emission of ammonia while producing granular urea by the urea granulation equipment, wherein the production method comprises (1) a step in which an aqueous solution containing urea, ammonia and carbon dioxide is introduced into a first stripper and subjected to stripping, thereby separating and recovering ammonia and carbon dioxide in the aqueous solution, and the aqueous solution after stripping is introduced into a urea hydrolyzer, (2) a step in which the aqueous solution introduced into the urea hydrolyzer is heated under pressure, thereby hydrolyzing urea in the aqueous solution, and the aqueous solution after hydrolysis is introduced into a second stripper, (3) a step in which the aqueous solution introduced into the second stripper is subjected to stripping, thereby separating ammonia and carbon dioxide in the aqueous solution, and (4) a step in which a part of the aqueous solution before being stripped in the first stripper, and/or, a part of the aqueous solution after being stripped in the first stripper but before being hydrolyzed in the urea hydrolyzer is introduced into an exhaust gas treatment equipment equipped with a urea dust scrubbing equipment and an equipment to suppress emission of ammonia.

Advantageous Effect of Invention

According to the present invention, since the amount of an aqueous solution to be introduced into the urea hydrolyzer is reduced, the load on the urea hydrolyzer and the second stripper is lowered. As a result, the amount of heating steam supplied to the urea hydrolyzer can be saved. At the same time, both equipments can be made compact. Note that the amount of steam that can be saved here mainly means the amount of heating steam supplied directly to the urea hydrolyzer or strippers, but in the case of applying heat using a heat exchanger instead of direct supply of heating steam, it also means the amount of heating steam supplied to the heat exchanger.

Further, even if an aqueous solution utilized as makeup water for an exhaust gas treatment equipment (for example, drainage resulting from the concentration step of a urea synthesis solution) contains ammonia, emission of ammonia into atmospheric air is suppressed since the exhaust gas treatment equipment has an equipment to suppress emission of ammonia.

MODES FOR CARRYING OUT THE INVENTION

Figure 1:
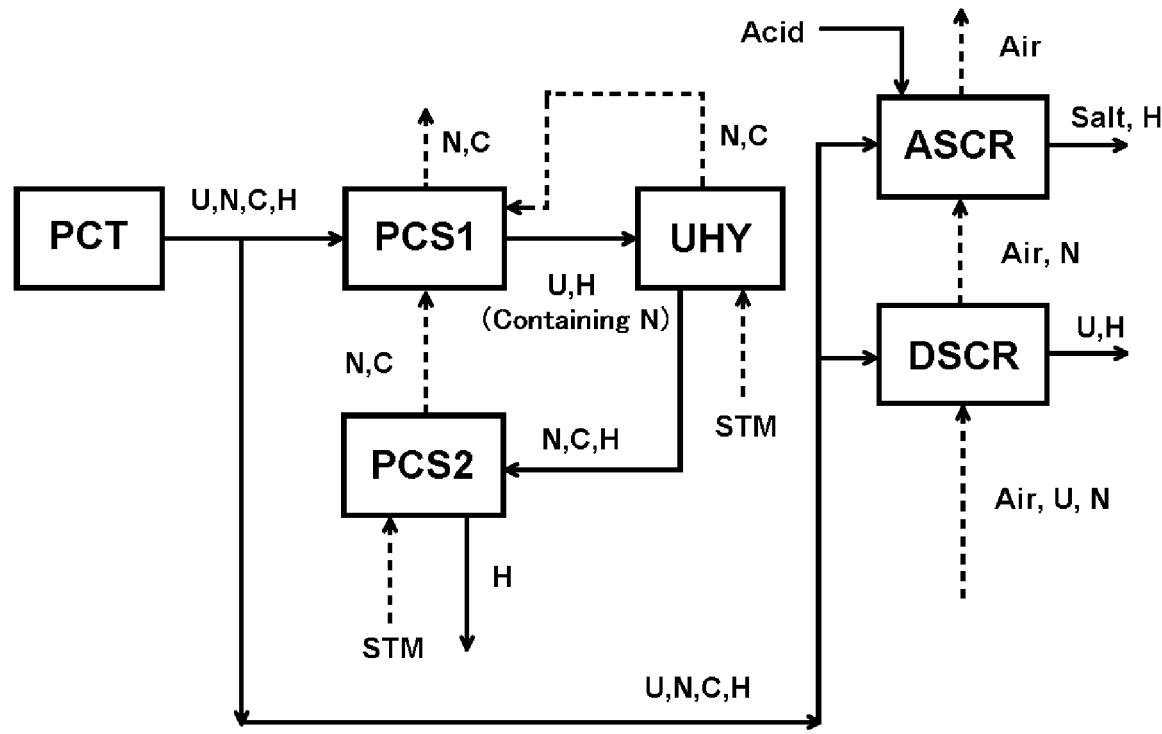
FIG. 1 is a flowchart showing one embodiment of each step of the treatment method of the present invention.

FIG. 1 is a flowchart showing one embodiment of each step of the treatment method of the present invention. In the embodiment shown in FIG. 1, first, a part of an aqueous solution consisting of urea (U), ammonia (N), carbon dioxide (C) and water (H) from a process condensate tank (PCT) (for example, drainage generated from the concentration step of a urea synthesis solution, hereinafter referred to simply as "aqueous solution") is introduced into a first stripper (PCS1), and the other part is used as makeup water for a urea dust scrubbing equipment (DSCR) and an ammonia scrubbing equipment (ASCR). This process is different from the treatment method of Patent Document 1 in which all of the aqueous solution from a process condensate tank (PCT) is introduced to a first stripper (PCS1). Of 100% by mass of the aqueous solution from the process condensate tank (PCT), the ratio of the aqueous solution (A) to be introduced into the first stripper (PCS1) to the aqueous solution (B) as makeup water for the urea dust scrubbing equipment (DSCR) and the ammonia scrubbing equipment (ASCR) (A:B) is determined depending on the urea dust scrubbing equipment (DSCR) and the ammonia scrubbing equipment (ASCR), and generally, it is 3:1 to 1:3.

Generally, the exhaust gas treatment equipment has a urea dust scrubbing equipment, but in many cases, it does not have an equipment to suppress emission ammonia. On the other hand, in the present invention, it is necessary that the exhaust gas treatment equipment has both a urea dust scrubbing equipment and an equipment to suppress emission of ammonia. In the embodiment shown in FIG. 1, the ammonia scrubbing equipment (ASCR) corresponds to an equipment to suppress emission of ammonia. A typical example of the ammonia scrubbing equipment (ASCR) is an acid scrubbing equipment. The acid scrubbing equipment is an equipment for circulating an acid-added aqueous solution inside to recover ammonia in the form of a salt. The type of the acid used for the acid scrubbing equipment is not particularly limited, but from the viewpoint of the ammonium salt generated, the acid is preferably selected from the group consisting of sulfuric acid, nitric acid, phosphoric acid and organic acids. However, the equipment to suppress emission of ammonia is not limited to this acid scrubbing equipment, and any equipment capable of suppressing the amount of ammonia in the discharged gas when discharged in the form of a gas is sufficient. For example, an equipment that suppresses emission of ammonia by passing an exhaust gas through a tower packed with a solid adsorbing ammonia may be used. Further, the equipment to suppress emission of ammonia may be an equipment to collect ammonia by adding an acid to an aqueous solution circulating in a urea dust scrubbing equipment (DSCR) or an equipment that suppresses emission of ammonia by adding an acid to an aqueous solution circulating in the other equipment than the urea dust scrubbing equipment (DSCR). Further, not only an exhaust gas discharged from a urea granulation step of a urea production equipment but also an exhaust gas containing ammonia generated from other steps may be introduced into the equipment to suppress emission of ammonia, and in this case, the equipment to suppress emission of ammonia will be shared in the urea granulation step and other steps.

The urea aqueous solution obtained in the urea dust scrubbing equipment (DSCR) is usually concentrated again in the concentration step to become product urea. A salt obtained in the ammonia scrubbing equipment (ASCR) or a mixed aqueous solution of the salt and urea may become a product different from urea, or can be mixed into the product of urea depending on the amount of the salt generated.

In the first stripper (PCS1) shown in FIG. 1, the introduced aqueous solution is subjected to stripping, thereby separating ammonia (N) and carbon dioxide (C) which are then discharged in the form of a gas. An aqueous solution consisting of urea (U) and water (H) after stripping (however, in practice, a trace amount of ammonia (N) also remains) is introduced into a urea hydrolyzer (UHY).

The urea (U) in the aqueous solution introduced into the urea hydrolyzer (UHY) is hydrolyzed to give ammonia (N) and carbon dioxide (C). Then, ammonia (N) and carbon dioxide (C) after hydrolysis are separated, returned to the first stripper (PCS1), and used as a stripping agent for the first stripper (PCS1). Further, the aqueous solution after hydrolysis is introduced into a second stripper (PCS2).

Ammonia and carbon dioxide separated by stripping in the second stripper (PCS2) are returned to the first stripper (PCS1), and used as a stripping agent for the first stripper (PCS1). Further, clean water obtained by separating ammonia and carbon dioxide is discharged outside the system and recovered.

Figure 2:
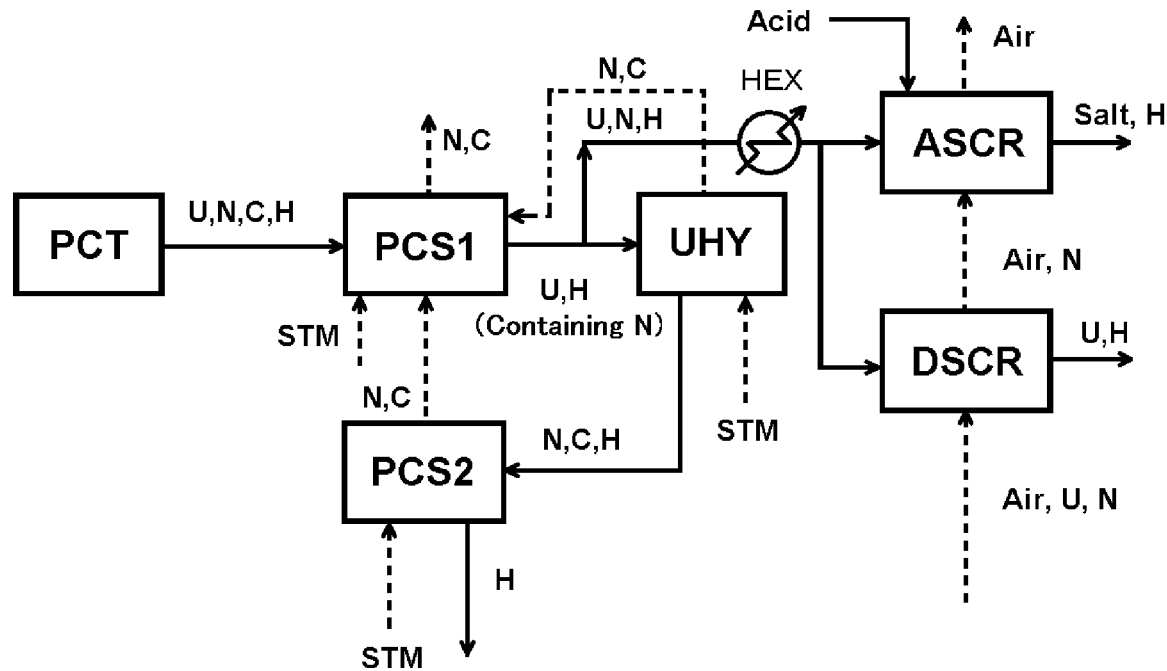
FIG. 2 is a flowchart showing another embodiment of each step of the treatment method of the present invention.
Figure 3:
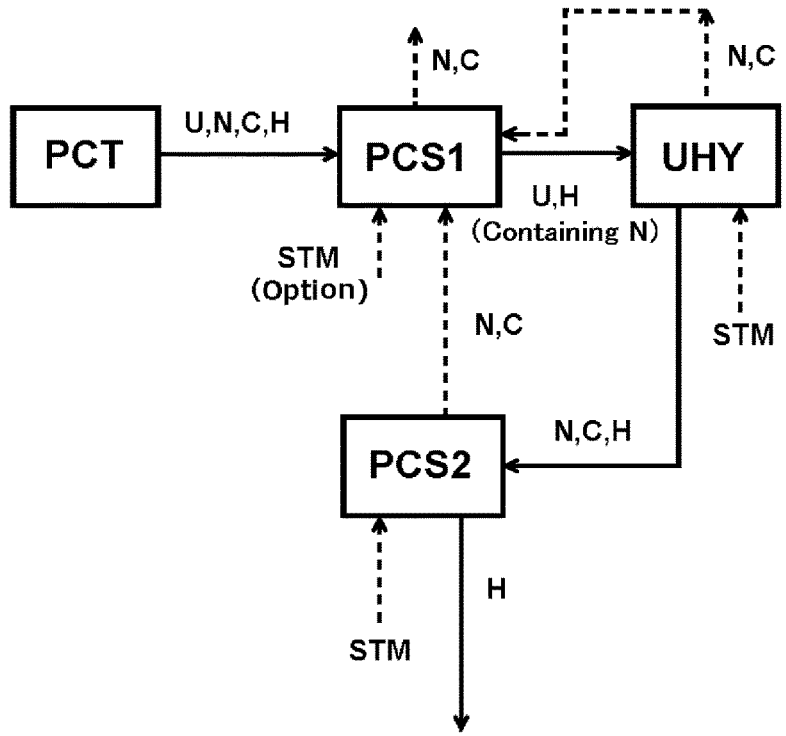
FIG. 3 is a flowchart showing each step of a conventional treatment method.

FIG. 2 is a flowchart showing another embodiment of each step of the treatment method of the present invention. In the embodiment shown in FIG. 2, all of the aqueous solution from a process condensate tank (PCT) is introduced into a first stripper (PCS1), a part of the aqueous solution after stripping in the first stripper (PCS1) is introduced into a urea hydrolyzer (UHY) and the other part is used as makeup water for a urea dust scrubbing equipment (DSCR) and an ammonia scrubbing equipment (ASCR). Of 100% by mass of the aqueous solution treated by the first stripper (PSC1), the ratio of the aqueous solution (A') to be introduced into the urea hydrolyzer (UHY) to the aqueous solution (B') as makeup water (A':B') is determined depending on the urea dust scrubbing equipment (DSCR) and the ammonia scrubbing equipment (ASCR), and generally, it is 3:1 to 1:3.

In the embodiment shown in FIG. 2, the temperature of the aqueous solution used as makeup water for the urea dust scrubbing equipment (DSCR) and the ammonia scrubbing equipment (ASCR) is lowered by a cooler (HEX). The reason for this is that since the temperature of the aqueous solution stripped in the first stripper (PCS1) is raised, if the aqueous solution is introduced into the urea dust scrubbing equipment (DSCR) and the ammonia scrubbing equipment (ASCR) as it is, the temperature in the equipments increases and hydrolysis of urea progresses during liquid transportation. A coolant used for the cooler is not restricted and may be cooling water or air, and heat may be recovered in the urea plant. As one embodiment of heat recovery in the urea plant, heat exchange with the aqueous solution supplied from the process condensate tank (PCT) to the first stripper (PCS1) is mentioned. In this case, the heat exchanger may be a shell-tube type heat exchanger or a plate type heat exchanger. Further, heat change between the aqueous solution after treatment extracted from the second stripper (PCS2) and the aqueous solution supplied from the process condensate tank (PCT) to the first stripper (PCS1) is a general method as shown in Patent Document 1, and this general heat change and heat change between the aqueous solution stripped in the first stripper (PCS1) and the aqueous solution supplied from the process condensate tank (PCT) to the first stripper (PCS1) may be conducted simultaneously. These heat exchanges may be performed in parallel or in series. Each heat exchange may be performed using different equipment or may be performed on one equipment. In addition, in the embodiment shown in FIG. 2, heating steam (STM) is supplied to the first stripper (PCS1), unlike the embodiment shown in FIG. 1. However, it is optional to supply heating steam (STM) to the first stripper (PCS1), and it may be supplied as required. When supplying heating steam (STM), if heating steam (STM) is placed on the stage below the stage where a gas from the second stripper (PCS2) is supplied to the first stripper (PCS1), it is easier to reduce the amount of ammonia contained in the aqueous solution after stripping in the first stripper (PCS1), depending on the supply amount of the steam.

In the embodiment shown in FIG. 2, the amount of an ammonium salt produced in the ammonia scrubbing equipment (ASCR) is smaller than that in the embodiment shown in FIG. 1, as demonstrated in examples described later.

As described above, not all but only a part of the aqueous solution from the process condensate tank (PCT) or the aqueous solution after stripping in the first stripper (PCS1) is introduced into a urea hydrolyzer (UHY), in the embodiments shown in FIGS. 1 and 2. Therefore, the amount of the aqueous solution to be treated in the urea hydrolyzer (UHY) reduces and the load of the urea hydrolyzer (UHY) decreases. As a result, it becomes possible to further reduce the amount of heating steam (STM) of high temperature and high pressure supplied to the urea hydrolyzer (UHY), and for example, in Example 1 described later, reduction to about 30% is made possible as compared with Comparative Example 1. At the same time, the loads of the first stripper (PCS1) and the second stripper (PCS2) are also reduced, in Example 1. As the loads of these equipments are reduced, the size of each equipment can be made compact, that is, in Example 1, the sizes of the first stripper (PCS1), the urea hydrolyzer (UHY) and the second stripper (PCS2) can be made compact until about 30% as compared with those in Comparative Example 1.

Figure 4:
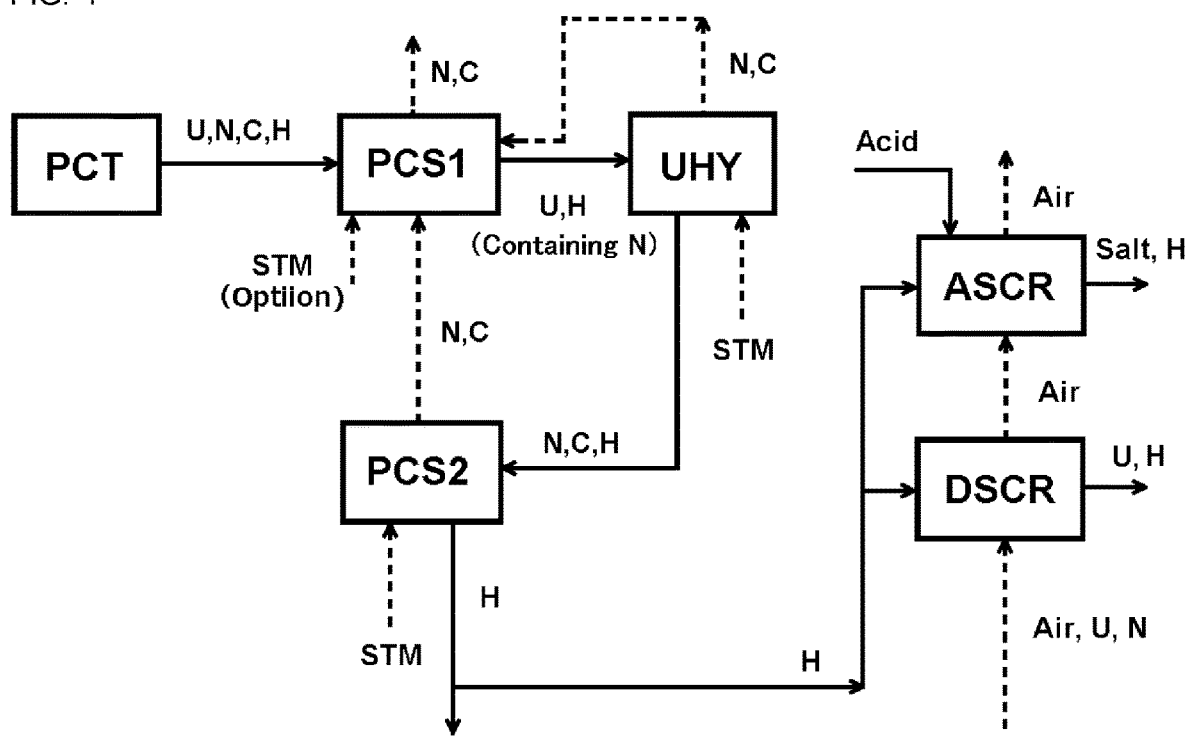
FIG. 4 is a flowchart showing a conventional example using clean water obtained by drainage treatment as makeup water.

FIG. 4 is a flowchart showing a conventional example using clean water obtained by drainage treatment as makeup water. In FIG. 4, a part of clean water after stripping in the second stripper (PCS2) is used as makeup water for the urea dust scrubbing equipment (DSCR) and the ammonia scrubbing equipment (ASCR), and this is a common method. On the other hand, the present invention is superior to such a general method in terms of reducing the heating steam amount and reducing the load of the equipment.

In the embodiments shown in FIGS. 1 and 2, urea (U) is contained in the aqueous solution from the process condensate tank (PCT) (FIG. 1) and the aqueous solution after stripping in the first stripper (PCS1) (FIG. 2), however, this point has no problem when these aqueous solutions are used for an exhaust gas treatment equipment. Further, though also ammonia (N) is contained in these aqueous solutions, this point has no problem since the exhaust gas treatment equipment has an ammonia scrubbing equipment (ASCR). The reason for this is that urea (U) in the aqueous solution is dissolved in the aqueous solution circulating in the ammonia scrubbing equipment (ASCR) and ammonia (N) in the aqueous solution becomes a salt for example by reaction with an acid, and the concentration of ammonia (N) in a gas to be discharged into atmospheric air can be reduced.

In the embodiment shown in FIGS. 1 and 2, either a part of the aqueous solution from the process condensate tank (PCT) (FIG. 1) or a part of the aqueous solution after stripping in the first stripper (PCS1) (FIG. 2) is used as makeup water, but the present invention is not limited to this. For example, using both as makeup water, the production amount of the ammonium salt may be adjusted. Furthermore, both a part of the aqueous solution from the process condensate tank (PCT) and a part of the aqueous solution with low ammonia concentration after stripping in the second stripper (PCS2) may be used as makeup water, or both a part of the aqueous solution after stripping in the first stripper (PCS1) and a part of the aqueous solution with low ammonia concentration after stripping in the second stripper (PCS2) may be used as makeup water. The embodiments using the aqueous solution with low ammonia concentration from the second stripper (PCS2) in combination as described above are preferable embodiments from the standpoint of controlling the production amount of the ammonium salt. Further, in the acid scrubbing equipment, usually a demister is installed. Since this demister is often installed in a place not in contact with the aqueous solution circulating inside to which an acid is added, emission of ammonia into atmospheric air can be suppressed by using a part of the aqueous solution with low ammonia concentration after stripping in the second stripper (PCS2) for washing of the demister, and this is a preferable embodiment.

In the embodiments shown in FIGS. 1 and 2, the urea dust scrubbing equipment (DSCR) and the ammonia scrubbing equipment (ASCR) are separately provided, but the present invention is not limited thereto. For example, by adding an acid to the makeup water of the urea dust scrubbing equipment (DSCR) so that ammonia can be recovered, they may be combined into one equipment. In this case, the equipment to suppress emission of ammonia will play roles of both the urea dust scrubbing equipment (DSCR) and the ammonia scrubbing equipment (ASCR) and will recover urea dust and ammonia.

Figure 5:
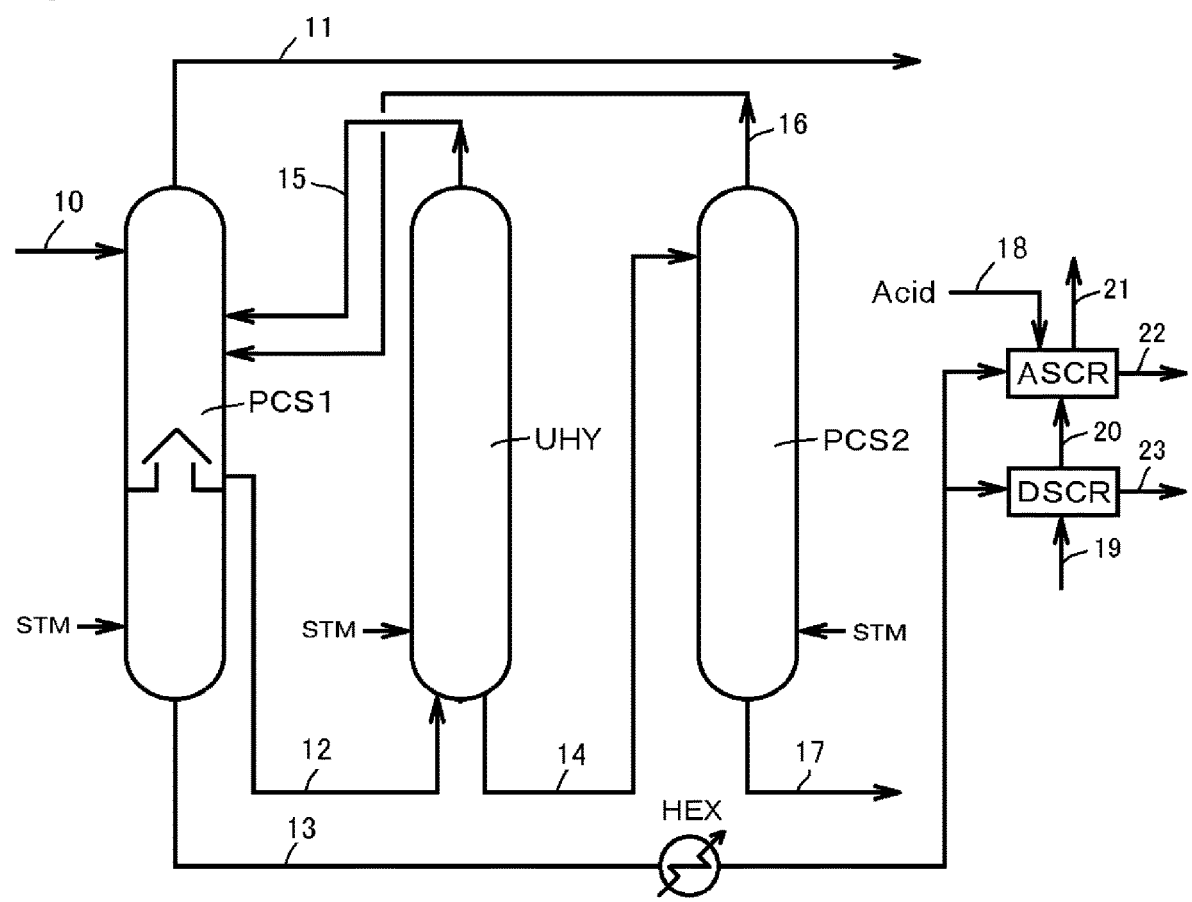
FIG. 5 is a schematic diagram showing one embodiment of the treatment equipment of the present invention.

FIG. 5 is a schematic diagram showing one embodiment of the treatment equipment of the present invention. In the embodiment shown in FIG. 5, the first stripper (PCS1), the urea hydrolyzer (UHY), the second stripper (PCS2), the urea dust scrubbing equipment (DSCR) and the ammonia scrubbing equipment (ASCR) are connected by pipes 10 to 23, to constitute a treatment equipment. This treatment equipment is a form suitable, for example, for implementing the treatment method shown in FIG. 2.

An aqueous solution containing urea, ammonia and carbon dioxide is introduced from the top of the first stripper (PCS1) through the pipe 10. The concentrations of urea, ammonia and carbon dioxide contained in this aqueous solution are not particularly limited. For example, the present invention is useful for treating drainage in the concentration step of a urea synthetic solution obtained by reacting ammonia and carbon dioxide under high temperature and high pressure, and in this case, the concentration of urea in the drainage is generally 0.1 to 5% by mass, especially 0.5 to 2% by mass. Further, the concentration of ammonia is generally 0.5 to 6% by mass, in particular 1 to 4% by mass. The concentration of carbon dioxide is generally 0.1 to 5% by mass, especially 0.5 to 2% by mass.

The temperature for stripping in the first stripper (PCS1) is preferably 120 to 160° C., more preferably 130 to 150° C. Further, the pressure is preferably 1 to 5 bar G, more preferably 2 to 4 bar G.

Ammonia and carbon dioxide separated in the first stripper (PCS1) are recovered as a gas from the top of the column through the pipe 11. This gas can be used, for example, as a heat source for removing unreacted substances contained in the urea synthesis solution, by introducing it into a low pressure decomposition column. In addition, the ammonia and carbon dioxide are eventually condensed in the absorber, for example, and can be used as the recovery liquid for synthesis of urea.

A part of the aqueous solution after stripping in the first stripper (PCS1) is introduced into the urea hydrolyzer (UHY) through the pipe 12 from the bottom and other part is introduced into the urea dust scrubbing equipment (DSCR) and the ammonia scrubbing equipment (ASCR) through the pipe 13.

Urea in the aqueous solution introduced into the urea hydrolyzer (UHY) is hydrolyzed to give ammonia and carbon dioxide. The reaction temperature in the urea hydrolyzer (UHY) is preferably 170 to 260° C., more preferably 180 to 230° C. The reaction pressure is preferably 7 to 47 bar G, more preferably 9 to 29 bar G. The residence time of the aqueous solution in the urea hydrolyzer is preferably 20 to 80 minutes, more preferably 40 to 60 minutes. Heating steam (STM) is introduced to the bottom of the urea hydrolyzer (UHY).

Then, the aqueous solution after hydrolysis in the urea hydrolyzer (UHY) is introduced from the bottom to the second stripper (PCS2) through the pipe 14. The concentration of residual urea in the aqueous solution after hydrolysis is preferably 5 ppm or less, more preferably 1 ppm or less. The ammonia concentration is preferably 5% by mass or less, more preferably 1% by mass or less. The concentration of carbon dioxide is preferably 5% by mass or less, more preferably 1% by mass or less. A gas generated from the urea hydrolyzer (UHY) is introduced into the first stripper (PCS1) from the top of the column through the pipe 15.

The temperature for stripping in the second stripper (PCS2) is preferably 120 to 160° C., more preferably 130 to 150° C. The pressure is preferably 1 to 5 bar G, more preferably 2 to 4 bar G. Heating steam (STM) is introduced to the bottom of the second stripper (PCS2). The amount of heating steam introduced is usually 1/10 or more, more preferably 1/5 or more, of the aqueous solution introduced into PCS2 through pipe 14.

Then, ammonia and carbon dioxide separated in the second stripper (PCS2) are introduced from the top of the column into the first stripper (PCS1) through the pipe 16. Further, clean water obtained by separating ammonia and carbon dioxide is recovered from the bottom through the pipe 17. The concentration of residual ammonia in the water is preferably 5 ppm or less, more preferably 1 ppm or less. Likewise, the concentration of residual urea in the water is preferably 1 ppm or less.

A part of the aqueous solution sent through the pipe 13 is introduced into the urea dust scrubbing equipment (DSCR) and the other part is introduced into the ammonia scrubbing equipment (ASCR), and both are used as makeup water. Air containing urea and ammonia discharged from the urea granulation step is introduced through the pipe 19 into the urea dust scrubbing equipment (DSCR) and brought into contact with the aqueous solution circulating through the urea dust scrubbing equipment (DSCR). Under this situation, most of urea in the air is dissolved in the aqueous solution, and ammonia is introduced together with the air into the ammonia scrubbing equipment (ASCR) through the pipe 20. An acid is supplied to the ammonia scrubbing equipment (ASCR) through the pipe 18, and the acidic aqueous solution circulates therein. Ammonia in the air reacts with this acid to become a salt and dissolves in the aqueous solution. As a result, the air with a reduced urea and ammonia concentration is discharged into atmospheric air through the pipe 21, and the aqueous solutions are discharged from the pipes 22, 23.

In the above explanations, a gas and an aqueous solution are transferred through pipes, for the sake of convenience, however, for example, the pipes 19 to 21 are usually in the form of a duct or an apparatus shell.

Further, the present invention is very useful as an improvement method to lower the load of the apparatus of an existing treatment equipment and to efficiently utilize a part of the aqueous solution. That is, if a pipe to introduce a part of the aqueous solution before being stripped in the first stripper, and/or, a part of the aqueous solution after being stripped in the first stripper but before being hydrolyzed in the urea hydrolyzer into an exhaust gas treatment equipment equipped with an ammonia scrubbing equipment, and, if necessary, other optional members or equipments, are added to an existing treatment equipment having a first stripper, a urea hydrolyzer and a second stripper, the amount of the aqueous solution introduced from the first stripper to the urea hydrolyzer is reduced, the loads of the urea hydrolyzer and the second stripper lower, and the amount of heating steam can be reduced. Further, even if the aqueous solution (e.g., drainage resulting from the concentration step of a urea synthesis solution) contains ammonia, emission of ammonia into atmospheric air is suppressed since the exhaust gas treatment equipment has an equipment to suppress emission of ammonia.

Further, the present invention is very useful in a production method of granular urea, comprising a step of producing granular urea by a urea granulation equipment and a step of introducing a gas containing urea dust and ammonia generated from the urea granulation equipment into an exhaust gas treatment equipment equipped with a urea dust scrubbing equipment and an equipment to suppress emission of ammonia. That is, when the aqueous solution generated from the concentration step of a urea synthesis solution (drainage) is treated by the treatment method of the present invention, the amount of the aqueous solution introduced from the first stripper to the urea hydrolyzer is reduced, the loads of the urea hydrolyzer and the second stripper lower, and the amount of heating steam can be reduced, since a part of the aqueous solution before being stripped in the first stripper, and/or, a part of the aqueous solution after being stripped in the first stripper but before being hydrolyzed in the urea hydrolyzer is introduced into an exhaust gas treatment equipment equipped with a urea dust scrubbing equipment and an equipment to suppress emission of ammonia. Further, even if the aqueous solution contains ammonia, emission of ammonia into atmospheric air is suppressed since the exhaust gas treatment equipment has an equipment to suppress emission of ammonia.

EXAMPLES

Hereinafter, the present invention will be described in more detail with reference to examples. However, the present invention is not limited by the examples.

Example 1 (FIG. 1)

From 35512 kg/hr of an aqueous solution discharged from a urea production equipment with a daily output of 2100 tons, which is an aqueous solution of 48° C. containing 414 kg/hr (1.17% by mass) of urea, 784 kg/hr (2.21% by mass) of ammonia and 491 kg/hr (1.38% by mass) of carbon dioxide, 25090 kg/hr of the aqueous solution is fed to a urea dust scrubbing equipment (DSCR) and an ammonia scrubbing equipment (ASCR) as makeup water and 10422 kg/hr of the aqueous solution is fed to a first stripper (PCS1).

The aqueous solution that is sent to the first stripper (PCS1) is pressurized by a pump, raised to 85° C. with a heat exchanger, and introduced to the top of the first stripper (PCS1) operating at 3 bar G. The top gas of the second stripper (PCS2) is introduced to the bottom of the first stripper (PCS1), and the top gas of the urea hydrolyzer (UHY) is supplied as the steam for stripping to the middle stage of the first stripper (PCS1). Ammonia and carbon dioxide in the aqueous solution are separated and the gas is discharged from the top of the column at 136° C. The composition of the discharged gas is shown as 299 kg/hr of ammonia, 233 kg/hr of carbon dioxide and 1799 kg/hr of steam. This gas is sent to a low pressure decomposition column in the urea production equipment and used as a heat source for removal of unreacted matters, and ammonia and carbon dioxide contained in the gas are finally absorbed into an aqueous solution by an absorber and recovered.

On the other hand, 11415 kg/hr of the stripped aqueous solution is discharged from the bottom of the first stripper (PCS1). The amount of the residual ammonia in this aqueous solution is reduced to 43 kg/hr (0.38% by mass). This aqueous solution is further pressurized by a pump and introduced to a urea hydrolyzer (UHY) operating at 23 bar G.

The urea hydrolyzer (UHY) is supplied with 749 kg/hr of heating steam of 40 bar G and 386° C. and heated to 210° C. and the residence time of the aqueous solution is set to 40 minutes. The amount of urea in the aqueous solution left the urea hydrolyzer (UHY) is 0 kg/hr, the amount of ammonia is 99 kg/hr and the amount of carbon dioxide is 18 kg/hr. This aqueous solution is depressurized by a pressure reducing valve and supplied to the second stripper (PCS2). Further, the gas generated from the urea hydrolyzer (UHY) is introduced to the middle stage of the first stripper (PCS1).

The aqueous solution is stripped by 2537 kg/hr of heating steam of 5 bar G introduced from the bottom of the second stripper (PCS2) and the treated aqueous solution is obtained from the bottom of the second stripper (PCS2). The concentrations of urea and ammonia in this treated aqueous solution lower to 1 ppm or less. This can be reused, for example, for boiler feed water. On the other hand, the mixed gas discharged from the top is introduced to the bottom of the first stripper (PCS1).

25090 kg/hr of the aqueous solution which is sent as makeup water to the urea dust scrubbing equipment (DSCR) and the ammonia scrubbing equipment (ASCR) is pressurized by a pump, and 21398 kg/hr thereof is sent to the urea dust scrubbing equipment (DSCR), and 3692 kg/hr thereof is sent to the ammonia scrubbing equipment (ASCR).

585480 $Nm^3$/hr of air containing 3500 kg/hr of urea and 58 kg/hr of ammonia discharged from the urea granulation step is introduced into the urea dust scrubbing equipment (DSCR) and brought into contact with the urea aqueous solution circulating in the urea dust scrubbing equipment (DSCR). Under this situation, most of urea in the air is dissolved in the aqueous solution, a part of water in the urea aqueous solution is evaporated, and the introduced ammonia contained in the air and the aqueous solution is entrained in air. The urea aqueous solution is concentrated to 45% by mass in the urea dust scrubbing equipment (DSCR), and 8273 kg/hr of the aqueous solution is withdrawn from the urea dust scrubbing equipment (DSCR).

1765 kg/hr of 98% by mass sulfuric acid is supplied to the ammonia scrubbing equipment (ASCR) to keep the ammonium sulfate aqueous solution acidic.

The air brought into contact with the urea aqueous solution in the urea dust scrubbing equipment (DSCR) is introduced into the ammonia scrubbing equipment (ASCR) and brought into contact with the ammonium sulfate aqueous solution circulating in the ammonia scrubbing equipment (ASCR). Under this situation, urea entrained in air is dissolved in the aqueous solution, and further, ammonia in air reacts with sulfuric acid to give ammonium sulfate, which is dissolved in the aqueous solution. At this time, the amount of urea contained in the exhaust gas generated from the ammonia scrubbing equipment (ASCR) is reduced to 17 kg (30 mg/$Nm^3$), and ammonia to 18 kg (30 mg/$Nm^3$). The water content of the ammonium sulfate aqueous solution becomes 60% by mass by makeup water in the ammonia scrubbing equipment (ASCR), and 5925 kg/hr of the aqueous solution is withdrawn from the ammonia scrubbing equipment (ASCR).

Example 2 (FIG. 2)

35512 kg/hr of an aqueous solution discharged from a urea production equipment with a daily output of 2100 tons, which is an aqueous solution of 48° C. containing 414 kg/hr (1.17% by mass) of urea, 784 kg/hr (2.21% by mass) of ammonia and 491 kg/hr (1.38% by mass) of carbon dioxide is pressurized by a pump, heated to 85° C. by a heat exchanger and introduced to the top of the first stripper (PCS1) operated at 3 bar G.

The top gas of the second stripper (PCS2) is introduced to the middle stage of the first stripper (PCS1), and the top gas of the urea hydrolyzer (UHY) is supplied as the steam for stripping to the middle stage. In addition, 2180 kg/hr of the steam for stripping is supplied to the bottom. Ammonia and carbon dioxide in the aqueous solution are separated and the gas is discharged from the top of the column at 132° C. The composition of the discharged gas is shown as 809 kg/hr of ammonia, 623 kg/hr of carbon dioxide and 2752 kg/hr of steam. This gas is sent to a low pressure decomposition column in the urea factory and used as a heat source for removal of unreacted matters, and ammonia and carbon dioxide contained in the gas are finally absorbed into an aqueous solution by an absorber and recovered.

On the other hand, the stripped aqueous solution is discharged from the bottom of the first stripper (PCS1). The amount of the residual ammonia in this aqueous solution is reduced to 146 kg/hr (0.38% by mass).

From 38765 kg/hr of the stripped aqueous solution, 21415 kg/hr of the stripped aqueous solution is sent as makeup water to the urea dust scrubbing equipment (DSCR) and the ammonia scrubbing equipment (ASCR), and 17351 kg/hr of the stripped aqueous solution is sent to the urea hydrolyzer (UHY).

17351 kg/hr of the stripped aqueous solution discharged from the bottom of the first stripper (PCS1) to be sent to the urea hydrolyzer (UHY) is further pressurized by a pump and introduced into the urea hydrolyzer (UHY) operated at 23 bar G.

The urea hydrolyzer (UHY) is supplied with 1144 kg/hr of heating steam of 40 bar G and 386° C. and heated to 210° C., and the residence time of the aqueous solution is set to 40 minutes. The amount of urea in the aqueous solution left the urea hydrolyzer (UHY) is 0 kg/hr, the amount of ammonia is 150 kg/hr and the amount of carbon dioxide is 28 kg/hr. This aqueous solution is depressurized by a pressure reducing valve and supplied to the second stripper (PCS2). Further, the gas generated from the urea hydrolyzer (UHY) is introduced into the first stripper (PCS1).

The aqueous solution is stripped by 4060 kg/hr of heating steam of 5 bar G introduced from the bottom of the second stripper (PCS2), and the treated aqueous solution is obtained from the bottom of the second stripper (PCS2). The concentrations of urea and ammonia in this treated aqueous solution lower to 1 ppm or less. This can be reused, for example, for boiler feed water. On the other hand, the mixed gas discharged from the top is introduced to the bottom of the first stripper (PCS1).

21415 kg/hr of the aqueous solution that is sent as makeup water to the urea dust scrubbing equipment (DSCR) and the ammonia scrubbing equipment (ASCR) is cooled by a cooler, and pressurized by a pump, and 20683 kg/hr thereof is sent to the urea dust scrubbing equipment (DSCR), and 732 kg/hr thereof is sent to the ammonia scrubbing equipment (ASCR).

585480 Nm$^3$/hr of air containing 3500 kg/hr of urea and 58 kg/hr of ammonia discharged from the urea granulation step is introduced into the urea dust scrubbing equipment (DSCR) and brought into contact with the urea aqueous solution circulating in the urea dust scrubbing equipment (DSCR). Under this situation, most of urea in the air is dissolved in the aqueous solution, a part of water in the urea aqueous solution is evaporated, and the introduced ammonia contained in the air and the aqueous solution is entrained in air. The urea aqueous solution is concentrated to 45% by mass in the urea dust scrubbing equipment (DSCR), and 8211 kg/hr of the aqueous solution is withdrawn from the urea dust scrubbing equipment (DSCR).

363 kg/hr of 98% by mass sulfuric acid is supplied to the ammonia scrubbing equipment (ASCR) to keep the ammonium sulfate aqueous solution acidic.

The air brought into contact with the urea aqueous solution in the urea dust scrubbing equipment (DSCR) is introduced into the ammonia scrubbing equipment (ASCR) and brought into contact with the ammonium sulfate aqueous solution circulating in the ammonia scrubbing equipment (ASCR). Under this situation, urea entrained in air is dissolved in the aqueous solution, and further, ammonia in air reacts with sulfuric acid to give ammonium sulfate, which is dissolved in the aqueous solution. At this time, the amount of urea contained in the exhaust gas generated from the ammonia scrubbing equipment (ASCR) is reduced to 17 kg (30 mg/Nm$^3$), and ammonia to 18 kg (30 mg/Nm$^3$).

The water content of the ammonium sulfate aqueous solution becomes 60% by mass by makeup water in the ammonia scrubbing equipment (ASCR), and 1215 kg/hr of the aqueous solution is withdrawn from the ammonia scrubbing equipment (ASCR).

Comparative Example 1 (FIG. 4)

35512 kg/hr of an aqueous solution discharged from a urea production equipment with a daily output of 2100 tons, which is an aqueous solution of 48° C. containing 414 kg/hr (1.17% by mass) of urea, 784 kg/hr (2.21% by mass) of ammonia and 491 kg/hr (1.38% by mass) of carbon dioxide is sent to the first stripper (PCS1).

The aqueous solution that is sent to the first stripper (PCS1) is pressurized by a pump, raised to 85° C. with a heat exchanger, and introduced to the top of the first stripper (PCS1) operating at 3 bar G. The top gas of the second stripper (PCS2) is introduced to the bottom of the first stripper (PCS1), and the top gas of the urea hydrolyzer (UHY) is supplied as the steam for stripping to the middle stage of the first stripper (PCS1). Ammonia and carbon dioxide in the aqueous solution are separated and the gas is discharged from the top of the column at 136° C. The composition of the discharged gas is shown as 1019 kg/hr of ammonia, 794 kg/hr of carbon dioxide and 6148 kg/hr of steam. This gas is sent to a low pressure decomposition column in the urea factory and used as a heat source for removal of unreacted matters, and ammonia and carbon dioxide contained in the gas are finally absorbed into an aqueous solution by an absorber and recovered.

On the other hand, the stripped aqueous solution is discharged from the bottom of the first stripper (PCS1). The amount of the residual ammonia in this aqueous solution is reduced to 147 kg/hr (0.38% by mass).

38897 kg/hr of the stripped aqueous solution discharged from the bottom of the first stripper (PCS1) is further pressurized by a pump and introduced into the urea hydrolyzer (UHY) operated at 23 bar G.

The urea hydrolyzer (UHY) is supplied with 2559 kg/hr of heating steam of 40 bar G and 386° C. and heated to 210° C., and the residence time of the aqueous solution is set to 40 minutes. The amount of urea in the aqueous solution left the urea hydrolyzer (UHY) is 0 kg/hr, the amount of ammonia is 336 kg/hr and the amount of carbon dioxide is 63 kg/hr. This aqueous solution is depressurized by a pressure reducing valve and supplied to the second stripper (PCS2). Further, the gas generated from the urea hydrolyzer (UHY) is introduced to the middle stage of the first stripper (PCS1).

The aqueous solution is stripped by 8662 kg/hr of heating steam of 5 bar G introduced from the bottom of the second stripper (PCS2), and the treated aqueous solution is obtained from the bottom of the second stripper (PCS2). The concentrations of urea and ammonia in this treated aqueous solution lower to 1 ppm or less. This can be reused, for example, for boiler feed water. On the other hand, the mixed gas discharged from the top is introduced to the bottom of the first stripper (PCS1).

20618 kg/hr out of 38772 kg/hr of the treated liquid is sent as makeup water to urea dust scrubbing equipment (DSCR) and the ammonia scrubbing equipment (ASCR). 20618 kg/hr of the aqueous solution that is sent as makeup water is pressurized by a pump, and 20381 kg/hr thereof is sent to the urea dust scrubbing equipment (DSCR), and 237 kg/hr thereof is sent to the ammonia scrubbing equipment (ASCR).

585480 Nm$^3$/hr of air containing 3500 kg/hr of urea and 58 kg/hr of ammonia discharged from the urea granulation step is introduced into to the urea dust scrubbing equipment (DSCR) and brought into contact with the urea aqueous solution circulating the urea dust scrubbing equipment (DSCR). At this time, most of urea in the air is dissolved in the aqueous solution, a part of water in the urea aqueous solution is evaporated, and the introduced ammonia contained in air is entrained in air. The urea aqueous solution is concentrated to 45% by mass in the urea dust scrubbing equipment (DSCR), and 7719 kg/hr of the aqueous solution is withdrawn from the urea dust scrubbing equipment (DSCR).

121 kg/hr of 98% by mass sulfuric acid is supplied to the ammonia scrubbing equipment (ASCR) to keep the ammonium sulfate aqueous solution acidic.

The air brought into contact with the urea aqueous solution in the urea dust scrubbing equipment (DSCR) is introduced into the ammonia scrubbing equipment (ASCR) and brought into contact with the ammonium sulfate aqueous solution circulating in the ammonia scrubbing equipment (ASCR). Under this situation, urea entrained in air is dissolved in the aqueous solution, and further, ammonia in air reacts with sulfuric acid to give ammonium sulfate, which is dissolved in the aqueous solution. At this time, the amount of urea contained in the exhaust gas generated from the ammonia scrubbing equipment (ASCR) is reduced to 17 kg (30 mg/Nm$^3$), and ammonia to 18 kg (30 mg/Nm$^3$). The water content of the ammonium sulfate aqueous solution becomes 60% by mass by makeup water in the ammonia scrubbing equipment (ASCR), and 399 kg/hr of the aqueous solution is withdrawn from the ammonia scrubbing equipment (ASCR).

The results of Examples 1 and 2 and Comparative Example 1 are shown in Table 1.

TABLE 1

|  | Amount of steam (kg/hr) | | | | 60 wt % ammonium sulfate aqueous solution |
| --- | --- | --- | --- | --- | --- |
|  | PCS1 | PCS2 | UHY | Total | (kg/hr) |
| Example 1 | 0 | 2537 | 749 | 3286 | 5925 |
| Example 2 | 2180 | 4060 | 1144 | 7384 | 1215 |

TABLE 1-continued

|  | Amount of steam (kg/hr) | | | | 60 wt % ammonium sulfate aqueous solution |
| --- | --- | --- | --- | --- | --- |
|  | PCS1 | PCS2 | UHY | Total | (kg/hr) |
| Comparative Example 1 | 0 | 8662 | 2559 | 11221 | 399 |

<Evaluation>

In Examples 1 and 2, the amount of heating steam (STM) consumed in the treatment step can be reduced, as compared with Comparative Example 1. The amount of ammonium sulfate (ammonium salt) produced was the highest in Example 1. On the other hand, in Example 2, since the production amount of ammonium sulfate is relatively smaller, even if ammonium sulfate is mixed with the urea solution and granulated, the granulated urea can be shipped as a product urea satisfying the required product quality, and there is no need to treat ammonium sulfate as a by-product.

INDUSTRIAL APPLICABILITY

The treatment method and the treatment equipment of the present invention are very useful in various steps in the urea synthesis field such as a treatment of drainage from the concentration step of a urea synthesis solution, since it is possible to reduce the amount of heating steam and make the equipment compact by lowering the load of a urea hydrolyzer without lowering the hydrolysis efficiency of urea, and furthermore, emission of ammonia into atmospheric air is suppressed even if a part of the aqueous solution (for example, drainage generated from the concentration step of a urea synthesis solution) is introduced into an exhaust gas treatment equipment.

EXPLANATION OF NUMERALS

PCS 1: first stripper
PCS 2: second stripper
UHY: urea hydrolyzer
DSCR: urea dust scrubbing equipment
ASCR: ammonia scrubbing equipment
PCT: process condensate tank
HEX: cooler
STM: heating steam
U: urea
N: ammonia
C: carbon dioxide
H: water
10 to 23: pipe

The invention claimed is:

1. A treatment method of an aqueous solution containing urea, ammonia and carbon dioxide in which urea in the aqueous solution containing urea, ammonia and carbon dioxide is hydrolyzed, and ammonia and carbon dioxide in the aqueous solution are separated and recovered, wherein the treatment method comprises
   (1) a step in which an aqueous solution containing urea, ammonia and carbon dioxide is introduced into a first stripper and subjected to stripping, thereby separating and recovering ammonia and carbon dioxide in the aqueous solution, and the aqueous solution after stripping is introduced into a urea hydrolyzer,
   (2) a step in which the aqueous solution introduced into the urea hydrolyzer is heated under pressure, thereby hydrolyzing urea in the aqueous solution, and the aqueous solution after hydrolysis is introduced into a second stripper, (3) a step in which the aqueous solution introduced into the second stripper is subjected to stripping, thereby separating ammonia and carbon dioxide in the aqueous solution, and (4) a step in which a part of the aqueous solution before being stripped in the first stripper, and/or, a part of the aqueous solution after being stripped in the first stripper but before being hydrolyzed in the urea hydrolyzer is introduced into an exhaust gas treatment equipment equipped with a urea dust scrubbing equipment and an equipment to suppress emission of ammonia.

2. The treatment method according to claim 1, wherein the equipment to suppress emission of ammonia is an equipment to suppress emission of ammonia by adding an acid to an aqueous solution circulating in the urea dust scrubbing equipment.

3. The treatment method according to claim 2, wherein the acid is selected from the group consisting of sulfuric acid, nitric acid, phosphoric acid and organic acids.

4. The treatment method according to claim 1, wherein the equipment to suppress emission of ammonia is an equipment to suppress emission of ammonia by adding an acid to an aqueous solution circulating in an ammonia scrubbing equipment.

5. The treatment method according to claim 4, wherein the acid is selected from the group consisting of sulfuric acid, nitric acid, phosphoric acid and organic acids.

6. The treatment method according to claim 1, wherein a part of the aqueous solution after being stripped in the first stripper but before being hydrolyzed in the urea hydrolyzer is cooled before being introduced into the exhaust gas treatment equipment.

7. The treatment method according to claim 2, wherein a part of the aqueous solution after being stripped in the first stripper but before being hydrolyzed in the urea hydrolyzer is cooled before being introduced into the exhaust gas treatment equipment.

8. The treatment method according to claim 3, wherein a part of the aqueous solution after being stripped in the first stripper but before being hydrolyzed in the urea hydrolyzer is cooled before being introduced into the exhaust gas treatment equipment.

9. The treatment method according to claim 4, wherein a part of the aqueous solution after being stripped in the first stripper but before being hydrolyzed in the urea hydrolyzer is cooled before being introduced into the exhaust gas treatment equipment.

10. The treatment method according to claim 5, wherein a part of the aqueous solution after being stripped in the first stripper but before being hydrolyzed in the urea hydrolyzer is cooled before being introduced into the exhaust gas treatment equipment.

11. A treatment equipment of an aqueous solution containing urea, ammonia and carbon dioxide in which urea in the aqueous solution containing urea, ammonia and carbon dioxide is hydrolyzed, and ammonia and carbon dioxide in the aqueous solution are separated and recovered, wherein the treatment equipment has a first stripper to subject an aqueous solution containing urea, ammonia and carbon dioxide to stripping, thereby separating ammonia and carbon dioxide in the aqueous solution, a pipe to recover a gas containing ammonia and carbon dioxide separated by stripping in the first stripper, a pipe to introduce the aqueous solution after stripping in the first stripper into a urea hydrolyzer, a urea hydrolyzer to heat under pressure the aqueous solution after stripping introduced from the first stripper, thereby hydrolyzing urea in the aqueous solution, a pipe to introduce the aqueous solution after hydrolysis in the urea hydrolyzer into a second stripper, a second stripper to subject the aqueous solution after hydrolysis in the urea hydrolyzer to stripping, thereby separating ammonia and carbon dioxide in the aqueous solution, and a pipe that introduces a part of the aqueous solution before being stripped in the first stripper into exhaust gas treatment equipment equipped with urea dust scrubbing equipment and equipment to suppress emission of ammonia, and/or, a pipe that introduces a part of the aqueous solution after being stripped in the first stripper but before being hydrolyzed in the urea hydrolyzer into exhaust gas treatment equipment equipped with urea dust scrubbing equipment and equipment to suppress emission of ammonia.

12. The treatment equipment according to claim 11, wherein the equipment to suppress emission of ammonia is an equipment to suppress emission of ammonia by adding an acid to an aqueous solution circulating in the urea dust scrubbing equipment.

13. The treatment equipment according to claim 12, wherein the acid is selected from the group consisting of sulfuric acid, nitric acid, phosphoric acid and organic acids.

14. The treatment equipment according to claim 11, wherein the equipment to suppress emission of ammonia is an equipment to suppress emission of ammonia by adding an acid to an aqueous solution circulating in an ammonia scrubbing equipment.

15. The treatment equipment according to claim 14, wherein the acid is selected from the group consisting of sulfuric acid, nitric acid, phosphoric acid and organic acids.

16. The treatment equipment according to claim 11, wherein the treatment equipment has a cooler for cooling a part of the aqueous solution after being stripped in the first stripper but before being hydrolyzed in the urea hydrolyzer, before the part of the aqueous solution is introduced into the exhaust gas treatment equipment.

17. The treatment equipment according to claim 12, wherein the treatment equipment has a cooler for cooling a part of the aqueous solution after being stripped in the first stripper but before being hydrolyzed in the urea hydrolyzer, before the part of the aqueous solution is introduced into the exhaust gas treatment equipment.

18. The treatment equipment according to claim 13, wherein the treatment equipment has a cooler for cooling a part of the aqueous solution after being stripped in the first stripper but before being hydrolyzed in the urea hydrolyzer, before the part of the aqueous solution is introduced into the exhaust gas treatment equipment.

19. The treatment equipment according to claim 14, wherein the treatment equipment has a cooler for cooling a part of the aqueous solution after being stripped in the first stripper but before being hydrolyzed in the urea hydrolyzer, before the part of the aqueous solution is introduced into the exhaust gas treatment equipment.

20. The treatment equipment according to claim 15, wherein the treatment equipment has a cooler for cooling a part of the aqueous solution after being stripped in the first stripper but before being hydrolyzed in the urea hydrolyzer, before the part of the aqueous solution is introduced into the exhaust gas treatment equipment.

21. An improvement method of a treatment equipment of an aqueous solution containing urea, ammonia and carbon dioxide, to lower the equipment load of the treatment equipment in which urea in the aqueous solution containing urea, ammonia and carbon dioxide is hydrolyzed and ammonia and carbon dioxide in the aqueous solution are separated and recovered, and to effectively utilize a part of the aqueous solution, wherein an existing treatment equipment has a first stripper to subject an aqueous solution containing urea, ammonia and carbon dioxide to stripping, thereby separating ammonia and carbon dioxide in the aqueous solution, a urea hydrolyzer to heat under pressure the aqueous solution after stripping introduced from the first stripper, thereby hydrolyzing urea in the aqueous solution, and a second stripper to subject the aqueous solution after hydrolysis in the urea hydrolyzer to stripping, thereby separating ammonia and carbon dioxide in the aqueous solution; and, the improvement method comprises adding a pipe to the existing treatment equipment in which the pipe introduces at least a part of the aqueous solution before being stripped in the first stripper into exhaust gas treatment equipment equipped with urea dust scrubbing equipment and equipment to suppress emission of ammonia, and/or, adding a pipe to the existing treatment equipment in which the pipe introduces a part of the aqueous solution after being stripped in the first stripper but before being hydrolyzed in the urea hydrolyzer into exhaust gas treatment equipment equipped with urea dust scrubbing equipment and equipment to suppress emission of ammonia.

22. A production method of granular urea which comprises a step of introducing a gas containing urea dust and ammonia generated from a urea granulation equipment into an exhaust gas treatment equipment equipped with a urea dust scrubbing equipment and an equipment to suppress emission of ammonia while producing granular urea by the urea granulation equipment, wherein the production method comprises (1) a step in which an aqueous solution containing urea, ammonia and carbon dioxide is introduced into a first stripper and subjected to stripping, thereby separating and recovering ammonia and carbon dioxide in the aqueous solution, and the aqueous solution after stripping is introduced into a urea hydrolyzer, (2) a step in which the aqueous solution introduced into the urea hydrolyzer is heated under pressure, thereby hydrolyzing urea in the aqueous solution, and the aqueous solution after hydrolysis is introduced into a second stripper, (3) a step in which the aqueous solution introduced into the second stripper is subjected to stripping, thereby separating ammonia and carbon dioxide in the aqueous solution, and (4) a step in which a part of the aqueous solution before being stripped in the first stripper, and/or, a part of the aqueous solution after being stripped in the first stripper but before being hydrolyzed in the urea hydrolyzer is introduced into an exhaust gas treatment equipment equipped with a urea dust scrubbing equipment and an equipment to suppress emission of ammonia.

* * * * *